(12) United States Patent
Wendl et al.

(10) Patent No.: US 8,046,239 B2
(45) Date of Patent: Oct. 25, 2011

(54) TIME MANAGEMENT SYSTEM FOR MEDICAL APPLICATIONS, PARTICULARLY IN A HOSPITAL SETTING

(75) Inventors: Udo Wendl, Hemhofen (DE); Heintje Wyczisk, Erlangen (DE)

(73) Assignee: Siemens Aktiengesellschaft (DE)

( * ) Notice: Subject to any disclaimer, the term of this patent is extended or adjusted under 35 U.S.C. 154(b) by 1682 days.

(21) Appl. No.: 11/169,217

(22) Filed: Jun. 28, 2005

(65) Prior Publication Data

US 2006/0004606 A1    Jan. 5, 2006

(30) Foreign Application Priority Data

Jun. 30, 2004   (DE) .................. 10 2004 031 690
Apr. 12, 2005   (DE) .................. 10 2005 016 852

(51) Int. Cl.
*G06Q 50/00* (2006.01)
(52) U.S. Cl. ................. 705/2; 705/3; 705/7.12
(58) Field of Classification Search .......... 705/2–3, 705/7; 600/300
See application file for complete search history.

(56) References Cited

U.S. PATENT DOCUMENTS

| | | | | |
|---|---|---|---|---|
| 5,065,315 A * | 11/1991 | Garcia | ............... | 705/2 |
| 5,153,919 A * | 10/1992 | Reeds et al. | ............... | 380/44 |
| 6,345,260 B1 * | 2/2002 | Cummings et al. | ............... | 705/8 |
| 6,389,454 B1 * | 5/2002 | Ralston et al. | ............... | 709/204 |
| 6,421,649 B1 * | 7/2002 | Rattner | ............... | 705/2 |
| 2002/0059082 A1 * | 5/2002 | Moczygemba | ............... | 705/3 |
| 2002/0131572 A1 * | 9/2002 | Paradis | ............... | 379/200 |
| 2002/0177757 A1 * | 11/2002 | Britton | ............... | 600/300 |
| 2002/0188179 A1 * | 12/2002 | Bulat | ............... | 600/300 |
| 2002/0188478 A1 * | 12/2002 | Breeland et al. | ............... | 705/3 |
| 2002/0191035 A1 * | 12/2002 | Selent | ............... | 345/866 |
| 2002/0198454 A1 * | 12/2002 | Seward et al. | ............... | 600/437 |
| 2003/0058110 A1 * | 3/2003 | Rich | ............... | 340/573.1 |
| 2003/0060691 A1 * | 3/2003 | Hiyama et al. | ............... | 600/300 |
| 2003/0069752 A1 * | 4/2003 | LeDain et al. | ............... | 705/2 |

(Continued)

FOREIGN PATENT DOCUMENTS

DE          199 55 211 A1      5/2001

(Continued)

OTHER PUBLICATIONS

A model for improving the quality and timeliness of compensation and pension . . . William Brinson Weeks; Peter Donald Mills; Julia Waldron; Steven Holloway Bro . . . Journal of Healthcare Management; Jul./Aug. 2003; 48, 4; ABI/INFORM Global p. 252.*

(Continued)

*Primary Examiner* — Gerald J. O'Connor
*Assistant Examiner* — Sind Phongsvirajati
(74) *Attorney, Agent, or Firm* — Lempia Summerfield Katz LLC

(57) ABSTRACT

For rationalizing medical treatments in the hospital setting, particularly for improving the utilization rate of examination and therapy equipment and to avoid long waiting times, a time management system (1) is disclosed having at least one treatment station (2a-2c) coupled with an appointment-scheduling module (3) for storing appointments (T1, T2) in memory, each of which is assigned to a medical procedure (8a-8c) specified with a view to the treatment station, or a defined treatment station, (2a-2c) and to a predetermined duration (tv). The treatment station (2a-2c) is operative to output a check-back signal (R) to the appointment-scheduling module (3) once a procedure (8a-8c) has been completely performed. The appointment-scheduling module (3) is embodied for dynamically adapting subsequent appointments (T2) on the basis of the check-back signal (R).

10 Claims, 3 Drawing Sheets

U.S. PATENT DOCUMENTS

| | | | |
|---|---|---|---|
| 2003/0206646 A1 | 11/2003 | Brackett | |
| 2003/0207227 A1* | 11/2003 | Abolfathi | 433/24 |
| 2003/0220817 A1* | 11/2003 | Larsen et al. | 705/2 |
| 2004/0019501 A1* | 1/2004 | White et al. | 705/2 |
| 2004/0088192 A1* | 5/2004 | Schmidt et al. | 705/3 |
| 2004/0111290 A1* | 6/2004 | Crane | 705/2 |
| 2004/0120557 A1* | 6/2004 | Sabol et al. | 382/128 |
| 2004/0122703 A1* | 6/2004 | Walker et al. | 705/2 |
| 2004/0122790 A1* | 6/2004 | Walker et al. | 707/1 |
| 2004/0243435 A1* | 12/2004 | Williams | 705/2 |
| 2004/0267575 A1* | 12/2004 | Boing | 705/3 |
| 2005/0027580 A1* | 2/2005 | Crici et al. | 705/8 |

FOREIGN PATENT DOCUMENTS

| | | |
|---|---|---|
| DE | 101 19 760 A1 | 10/2001 |
| DE | 101 25 504 A1 | 12/2002 |
| WO | WO 2004/042563 A2 | 5/2004 |

OTHER PUBLICATIONS

Get organized! Practice management software Anonymous Dental Products Report; Sep. 2002; 36, 9; ProQuest Health and Medical Complete p. 122.*

Improving appointment scheduling for medical screening Rose D. Baker; Paula L. Atherill IMA Journal of Management Mathematics; Oct. 2002; 13, 4; Research Library p. 225.*

Market Source Anonymous Health Management Technology; Nov. 1999; 20, 10; ABI/INFORM Global p. 60.*

Stephen D Mallard, Terri Leakeas, W Jack Duncan, Michael E Fleenor, Richard J Sinsky. Journal of Public Health Management and Practice. Frederick: Mar./Apr. 2004. vol. 10, Iss. 2; p. 148.*

Wang, Ben (2003). Capacity management in stochastic service systems. Ph.D. dissertation, Columbia University, United States—New York. Retrieved Feb. 25, 2009, from ABI/INFORM Global database. (Publication No. AAT 3074326).*

European Search Report 2004P05881EP dated Sep. 15, 2006 (in German).

European Examination Report 2004P05881EP dated Feb. 2, 2007 (in German).

Translation of Pertinent Portions of European Examination Report (EP 04 105 641.4-2201).

* cited by examiner

FIG 4
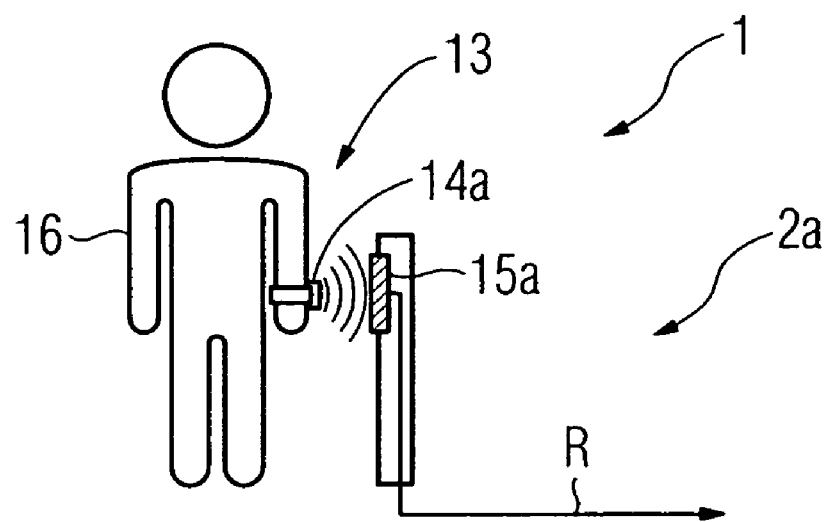
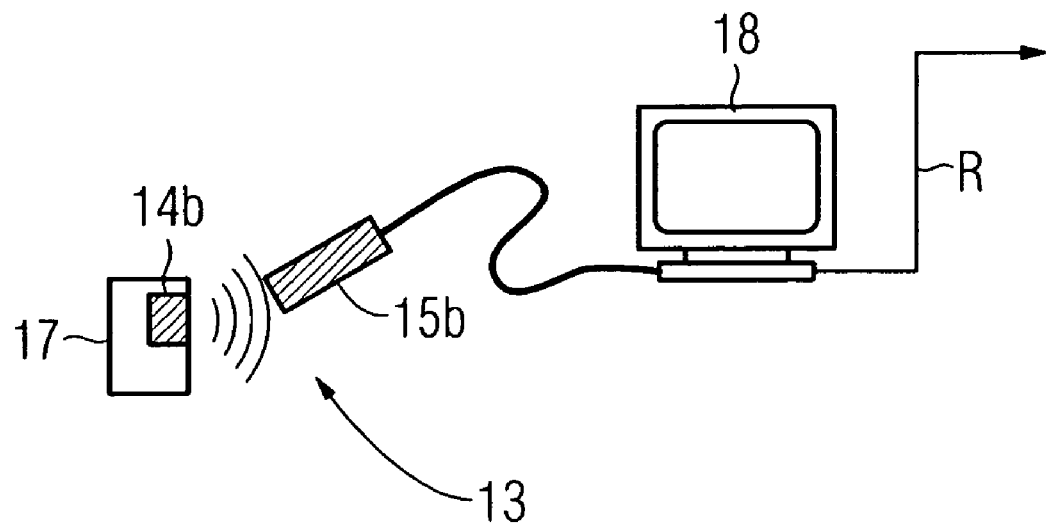

TIME MANAGEMENT SYSTEM FOR MEDICAL APPLICATIONS, PARTICULARLY IN A HOSPITAL SETTING

REFERENCE TO RELATED APPLICATIONS

This application is further related to and claims benefit of priority under 35 U.S.C. §119 to the filing date of Jun. 30, 2004 of German patent application no. 102004031690.2 DE, filed on Jun. 30, 2004 and the filing date of Apr. 12, 2005 of German patent application no. 102005016852.3 DE, filed on Apr. 12, 2005.

BACKGROUND

In the hospital setting, medical treatments are increasingly being defined in the form of standardized procedures (or work flows) in a way that is similar to industrial processes. As used here, the term "treatment" includes the entire field of medical treatments, especially diagnosis, therapy planning, and therapy. The efficiency of such standardization is increasingly significant, especially given the increasing cost pressure and hence the economy increasingly demanded of a hospital. Once standardized procedures have been predefined, they can be better planned for, and appointments for them can be set better. Unlike conventional industrial processes, however, such an appointment schedule is a rule difficult to achieve in a hospital setting. This can ascribed particularly to the fact that estimating the actual duration of a medical treatment in advance can be done only with comparatively great uncertainty, because of the individual differences of every patient examined and the associated clinical picture. In particular, findings that affect the duration of the treatment are typically not known until during the course of a treatment.

The resultant deviations from the original appointment schedule, depending on the direction of the deviation, lead to long waiting times for later patients or times when the examination equipment stands idle between two treatments, making for a comparatively low degree of utilization. Low utilization is a considerable disadvantage, above all in the case of a cost-intensive examination or treatment device, such as a particle accelerator used for therapeutic purposes.

Until now, for scheduling appointments in the hospital setting, a conventional, and in particular software-implemented, appointment scheduler with static time allocation has typically been employed. Such an appointment scheduler makes it possible to assign appointments within fixed or variable time slots. If deviations from the appointment schedule occur in practice, then the appointment schedule may need to be updated manually, which is complicated. If for reasons of time the manual updating is not done, then a delay, once it occurs, spreads on and on to newly assigned appointments.

BRIEF DESCRIPTION OF THE DRAWINGS

FIG. 4 shows a time management system according to an alternative embodiment.

DETAILED DESCRIPTION OF THE DRAWINGS AND PRESENTLY PREFERRED EMBODIMENTS

Figure 1:
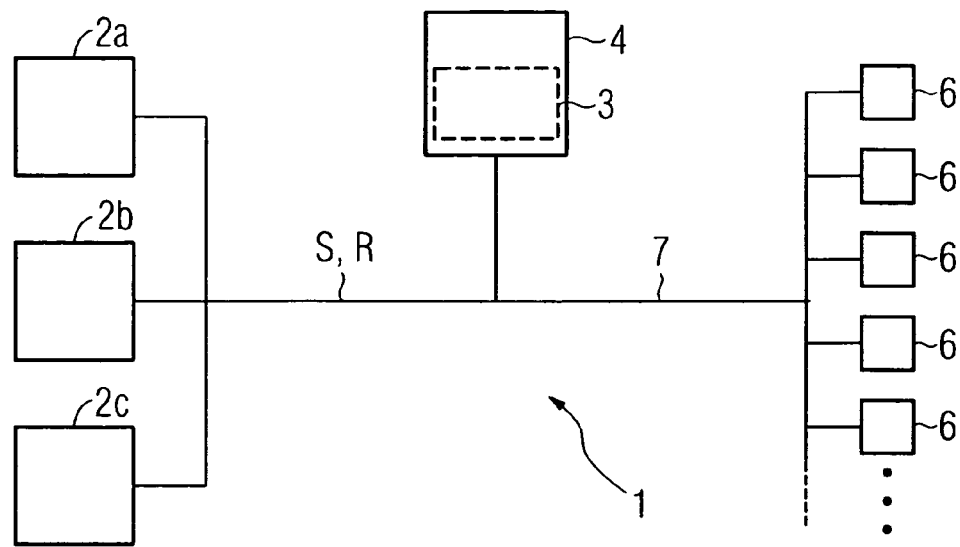
FIG. 1 is a schematic, simplified block circuit diagram of a time management system according to one embodiment.

The disclosed embodiments relate to a time management system for medical treatments intended particularly for use in a hospital. Accordingly, in one embodiment, the time management system includes at least one treatment station and an appointment-scheduling module. The treatment station may include a medical radiation therapy or examination system, such as a CT unit, some other kind of radiology unit, a magnetic resonance imaging system, or the like that is associated with a particle accelerator (linear accelerator, cyclotron or synchrotron). However, a computer assigned to a treatment room or operation room may also be provided as the treatment station. The appointment-scheduling module is preferably embodied as a software component of a data processing system connected to each treatment station within a data network. The appointment-scheduling module is embodied to store a number of appointments in memory, each being associated with one medical procedure. A scheme of a medical treatment, which in particular is specified with regard to an associated treatment station and a predetermined duration, that is, an average desired duration, is called a procedure. Making an appointment for such a procedure, that is, by generating an appointment for a certain procedure, assigns the procedure both a starting time and a patient to be examined. By means of the appointment and the associated procedure, the data essential to a medical treatment, particularly the starting time, predetermined duration, patient, type of treatment, and treatment station, are thus fixed.

According to one embodiment of the treatment station or each treatment station, when a procedure is completed in an appointment, the station will output a check-back signal to the appointment-scheduling module; the appointment-scheduling module is in turn embodied for dynamically adapting the starting times of subsequent appointments on the basis of the check-back signal. This includes, first, postponing appointments. If performing a procedure in an appointment takes longer than the specified time assigned to the procedure, then subsequent appointments are delayed accordingly, as a consequence of this dynamic adaptation. Conversely, if performing the procedure in an appointment takes less than the specified time, then subsequent appointments for the treatment station are moved up accordingly. Optionally, the series of appointments, or in the case of a plurality of equivalent treatment stations the treatment station assigned to a particular appointment, can be adapted as needed. It is also provided that the allocation of resources (such as the particle beam of a particle accelerator) and staffing planning for the treatment stations be adapted dynamically in accordance with the appointment schedule.

By means of the feedback of the treatment station, or each treatment station, to the appointment-scheduling module and the dynamic adaptation of the appointment schedule performed by the appointment-scheduling module, it is assured that the appointment schedule will be automatically updated continuously. As a result, on the one hand especially good utilization of the treatment stations is achieved, and on the other, long waiting times can be effectively avoided in this way. In particular, it can be assured in a simple way that the new assignment of appointments is always done with a view to an updated of the existing appointment schedule. This effectively prevents a delay, once it happens, from spreading to more and more new appointments in a chain reaction.

With a view to efficient, rational assignment of appointments, it is preferably provided that the appointment-scheduling module for the treatment station or each treatment station is specified at least one predefined procedure, which is already specified in advance in terms of the predetermined duration associated with it. Alternatively, however, at least for some procedures, it may be provided that the predetermined duration is defined only manually, and not until the appointment is made.

In a refinement of the time management system, it is provided that the procedure or each procedure is subdivided into a number of procedure steps. In this version, each treatment station is expediently embodied for displaying the completion of each procedure step in an appointment by outputting a corresponding check-back signal to the appointment-scheduling module, so that possibly even during an ongoing treatment, this module can react to any deviations from the original appointment schedule and adapt the appointment schedule accordingly.

In one embodiment, the time management system is embodied on the basis of the DICOM standard. The DICOM (Digital Imaging and Communications in Medicine) standard, which is internationally established in imaging medical technology, defines data objects, communications protocols, and server-client applications in the diagnostic field. For instance, data objects that represent an X-ray, CT, or MRI are defined. The standard further defines how these objects are forwarded, for instance from the imaging device (generator) to an evaluation device (workstation) or a digital archive. For further details, reference may be made to the documentation of the standard known as "Digital Imaging and Communications in Medicine (DICOM)", Version 3, Part 1 (PS 3.1-2003) through Part 16 (PS 3.16-2003), NEMA, Rosslyn, Va., USA. The server-client definition according to DICOM is supplemented by the IHE (Integrating the Healthcare Enterprise) standard, which provides the roles and objects with which the components involved in clinical processes, such as radiology information system (RIS), imaging device and evaluation station, are assigned their tasks in the process. For instance, the RIS can generate a list of patients to be examined. This list is retrieved by the imaging device along with the relevant patient data. Once the examination data has been recorded, as in an X-ray, the full information is forwarded to an interpretation station in the radiology department. The radiologist then dictates his findings. The images are stored in a digital archive. The RIS stores the findings in memory.

The DICOM standard now offers the possibility of defining not only already predetermined and internationally standardized procedures but also freely configurable procedures. These server-client applications are summarized under the term "General Purpose Worklist or General Purpose Procedure Steps (GPPS)." With GPPS, arbitrary processes in the hospital setting that are compatible with the DICOM standard can be described. For this purpose, DICOM furnishes especially the class of planned procedure steps, by means of which process steps to be performed can be defined. DICOM also makes the class of performed procedure steps available, by means of which the components involved in the clinical process can report that the planned procedure steps have been performed to a procedure step provider. With the aid of these object and communication definitions, which are available to all manufacturers through the DICOM standard, DICOM-compatible components can now furnish reports. The GPPS environment may be especially advantageously employed for achieving dynamically adaptive time management. To that end, it is provided that for making an appointment for a procedure, the appointment-scheduling module formulates the step, or every step, of the procedure in the form of a planned procedure step in accordance with DICOM and allocates it to the treatment station performed pertaining to the procedure. For achieving the check-back signal, it is expediently provided that the treatment station, or each treatment station, formulates every procedure step performed in the appointment in the form of a performed procedure step in accordance with DICOM and reports it back to the appointment-scheduling module. By monitoring these performed procedure steps reported back, simple adaptation of the appointment schedule is now possible.

In addition, or alternatively to this, for generating check-back signals, it is provided that a locating system, embodied for locating patients, transporting devices, or medical products, be used for locating purposes. In one embodiment, the locating system may be embodied on the basis of a bar code system. In an alternate embodiment, RFID (Radio Frequency Identification) or transponder technology is employed for generating check-back signals. The locating system includes at least one RFID signal transducer and at least one RFID reader unit, which generates the check-back signal when the RFID signal transducer, or an RFID signal transducer, is read out by the reader unit. The RFID signal transducer is embodied in particular as a mobile part and is assigned to a transporting device (such as a trolley), a medical product (as part of a package, as a label on a package, or the like), or directly to a patient (for instance in the form of an ID badge). RFID signal transducers or transponders can be affixed to the patient (on his arm or leg), to treatment aids (such as vacuum mattresses), or to the treatment table (gurney/cot, wheelchair). The reader units should be set up and oriented accordingly. The reader unit or each reader unit is conversely preferably stationary, that is, assigned to a certain place, so that once the associated RFID signal transducer is brought into the sphere of influence of a reader unit stationed at that place, the current position of the patient, transporting device, or product in a hospital is located. In particular, the reader units are mounted at different heights above the floor, so that signal transducers or transponders affixed to the arms and legs of patients who are standing or walking and patients who are lying down can be read in; for instance, on entering or leaving a treatment station, changing room, and so forth, by communication of the RFID signal transducer assigned to a patient with a corresponding reader unit, a check-back signal is generated automatically.

The check-back signal, generated from the association of place and time, is allocated to the procedure step by means of predefined medical procedures (work flow, procedure step), and based on that, an optimization of the appointment-making process is made by the appointment-scheduling module.

The process of making an appointment for a procedure is optionally done manually; the medical staff selects a predefined procedure that specifies the patient to be examined and in particular selects an assigned starting time for the appointment. The appointment-scheduling module is, however, preferably embodied for automatically selecting the time associated with the appointment and entering it in the appointment schedule, optionally after a positive acknowledgement from the medical staff. The appointment-scheduling module is embodied such that it selects the assigned starting time for the appointment on the specification of an optimized utilization of the associated treatment station. If there are a plurality of treatment stations that are dependent on joint resources, then it is expediently provided that the appointment-scheduling module associates the appointments of the various treatment stations with one another chronologically in such a way that the jointly used resources are equally utilized. If a delay occurs in the area of one treatment station, then the appointment-scheduling module expediently also adapts the later appointments of the other treatment stations accordingly. Optionally, appointments are made taking into account a static pre-correction that is derived from an evaluation of appointment changes that have already been made. For instance, if for a particular procedure, a delay statistically occurs with extraordinary frequency, then the appointment-scheduling module, in the future determination of this procedure, will schedule a longer length of time than the predetermined duration originally assigned to the procedure.

For better avoidance of waiting times, it is expediently provided that the appointment-scheduling module, upon a dynamic adaptation of an appointment, automatically informs the associated patient in accordance with predefined criteria. This can be done in the form of a direct message, such as an automatically generated call, an SMS, by means of a radio receiver (beeper), and so forth. Alternatively, however, the patient can be informed indirectly, for instance by informing the staff responsible for caring for the patient. It is also conceivable that the appointments can be made accessible to the patient, in always updated form, on a display board, information screen, or the like.

In addition or as an alternative, the patient for whom an appointment is made is automatically informed of this by the appointment-scheduling module, in advance of the time set for the appointment by a predetermined length of time, or lead time. This option is highly advantageous especially in the inpatient hospital setting, especially since then a patient can be called up within a relatively short time for treatment, so that waiting times can be avoided almost entirely.

One exemplary embodiment of the invention is described in further detail below in terms of a drawing. Elements and sizes corresponding to one another are identified by the same reference numerals throughout the drawings.

FIG. 1 is a schematic, simplified block circuit diagram of one embodiment of a time management system with an appointment-scheduling module, three treatment stations, and a number of communications units for communication with a patient. In FIG. 1, a time management system 1 which is intended particularly for use in a hospital is shown schematically. The time management system 1 includes three treatment stations 2a, 2b, 2c. The treatment stations 2a-2c involves medical therapy and examination equipment, such as an X-ray unit, a radiotherapy station of a particle accelerator, and a magnetic resonance or MRI unit. A computer assigned to an examination or operation room may also be a treatment station.

The time management system 1 further includes an appointment-scheduling module 3, which is embodied as a software component of a data processing system 4, such as a central server.

The time management system 1 furthermore has access to a number of communications units 6 for communicating with the patients. As the communications unit 6, a communications means by which a patient, or the medical staff caring for patients, can be spoken to directly can be used, such as a room or station telephone, cell phone, etc. However, a generally accessible information medium, such as a display board, information screen, or the like, may also be included as a communications unit 6.

The treatment stations 2a-2c, the data processing system 4 and the communications units 6 communicate with one another via a data transmission network 7. The data transmission network 7 may also include a plurality of separate networks, such as a LAN, a Tk network, and optionally wireless networks, etc.

Figure 2:
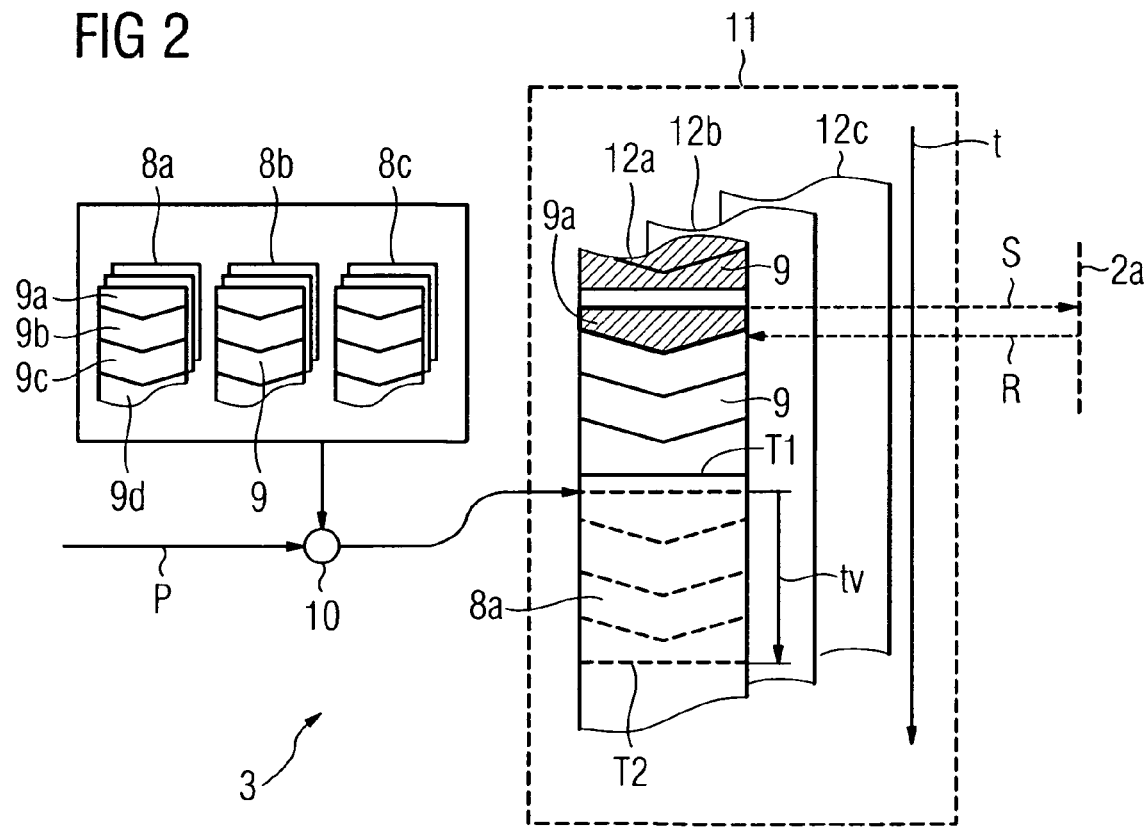
FIG. 2 is a simplified function chart of the appointment-scheduling module of FIG. 1 in making an appointment for a medical procedure.

The object of the appointment-scheduling module 3, shown in a function diagram in FIG. 2, is to coordinate treatment appointments of the patients at the treatment stations 2a-2c in such a way that the treatment stations 2a-2c are on the one hand utilized as well as possible, or in other words idle times during the usual treatment times are largely avoided, yet on the other hand long waiting times for the patients are to be avoided as well.

For that purpose, a number of predefined procedures 8a, 8b and 8c are specified to the appointment-scheduling module 3 for each treatment station 2a-2c. Each procedure 8a-8c represents the abstract scheme of a medical treatment that is intended to be performed at the associated treatment station 2a, 2b or 2c, respectively. If the treatment station 2a is for instance an X-ray unit, then among the procedures 8a associated with this treatment station 2a, one procedure 8a is for instance directed to a chest X-ray using the anterior-posterior projection for the image. If the treatment station 2b is a radiation therapy station, for instance, then an associated procedure 8b is for instance directed to a particular radiotherapy treatment.

Each procedure 8a-8c is in turn broken down into a number of procedure steps 9. The successive procedure steps 9a-9d of the procedure 8a include for instance registering a patient 9a, immobilizing him in the imaging position 9b, the actual imaging 9c, and finally remobilizing the patient 9d. A predetermined specified time, that is, an average desired time, is allocated to each procedure step 9, 9a-9d. From the total of the specified times allocated to the individual procedure steps 9, 9a-9d of a procedure 8a-8c, the result is in particular a (total) predetermined duration tv, which is schematically represented in FIG. 2 and is allocated to the appropriate procedure.

In the course of appointment scheduling, appointments for procedures 8a-8c are assigned by the appointment-scheduling module 3; that is, an appointment T1, T2 is assigned to a particular procedure 8a-8c. An appointment T1, T2 represents a concrete instance of an abstract procedure 8a-8c, by which the procedure 8a-8c is made concrete with regard to a particular patient and an assigned starting time ta. The appointment T1, T2 thus specifies all the information required for the concrete execution of a medical treatment corresponding to the applicable procedure 8a-8c.

For making an appointment for a procedure 8a-8c, the medical staff selects the particular procedure 8a-8c and specifies the patient to be examined by inputting corresponding patient data P that make it possible to identify the patient, such as the name of the patient or a code number corresponding to the patient, and so forth. The assigned starting time ta for the appointment T1, T2 is either also specified manually by the medical staff or automatically defined by an appointment-making module 10 of the appointment-scheduling module 3. The appointment-making module 10 then enters the appointment T1, T2 into an appointment schedule 11 of the appointment-scheduling module 3. The appointment schedule 11 is a calendar with a number of fields 12a-12c, each associated with one treatment station 2a, 2b or 2c. The time axis t of the calendar is represented schematically as an arrow in FIG. 2.

FIG. 2 schematically shows the setting of the appointment T2 that has been allocated to a procedure 8a associated with the treatment station 2a. The appointment T2 is correspondingly entered in the field 12a of the appointment schedule 11 such that it comes chronologically immediately after the last, already existing, appointment T1.

Optionally, once an appointment has been made, the appointment-making module 10 automatically informs the appropriate patient.

In addition to assigning appointments T1, T2, the appointment-scheduling module 3 controls and monitors the concrete performance of the corresponding procedures 8a-8c by the associated treatment stations 2a-2c. To that end, for each procedure step 9 performed in accordance with the appointment, the appointment-scheduling module 3 outputs a corresponding control signal S to the associated treatment station 2a-2c. Once this procedure step 9 has been performed, the treatment station 2a-2c sends a corresponding feedback signal R back to the appointment-scheduling module 3. By evaluating the check-back signals R, the appointment-scheduling module 3 can tell which procedure steps 9, 9a have already been performed (shown shaded in FIG. 2).

In one embodiment, the time management system 1 uses the classes of the so-called general purpose procedure steps (GPPS), defined by the DICOM standard, for forming the control signals S and check-back signals R. Accordingly, the appointment-scheduling module generates control signals S by formulating a procedure step to be performed (in FIG. 2, procedure step 9a of appointment T1 has been highlighted as an example) as a planned procedure step and makes it accessible to the treatment station 2a. Once the procedure step 9a has been performed on time, the treatment station 2a generates the check-back signal R as shown in FIG. 2 by formulating this procedure step as a performed procedure step and returns it to the appointment-scheduling module 3. In this respect, regardless of the manufacturer, each item of examination equipment that is GPPS-capable in the sense of the DICOM standard can be incorporated as a treatment station into the time management system 1.

On the basis of the check-back signal R, the appointment-scheduling module 3 checks whether the specified time, assigned to each procedure step 9 performed on time, was adhered to within predetermined tolerance limits. As long as that is the case, the appointment schedule 11 is recognized by the appointment-scheduling module 3 as having been adhered to.

Figure 3:
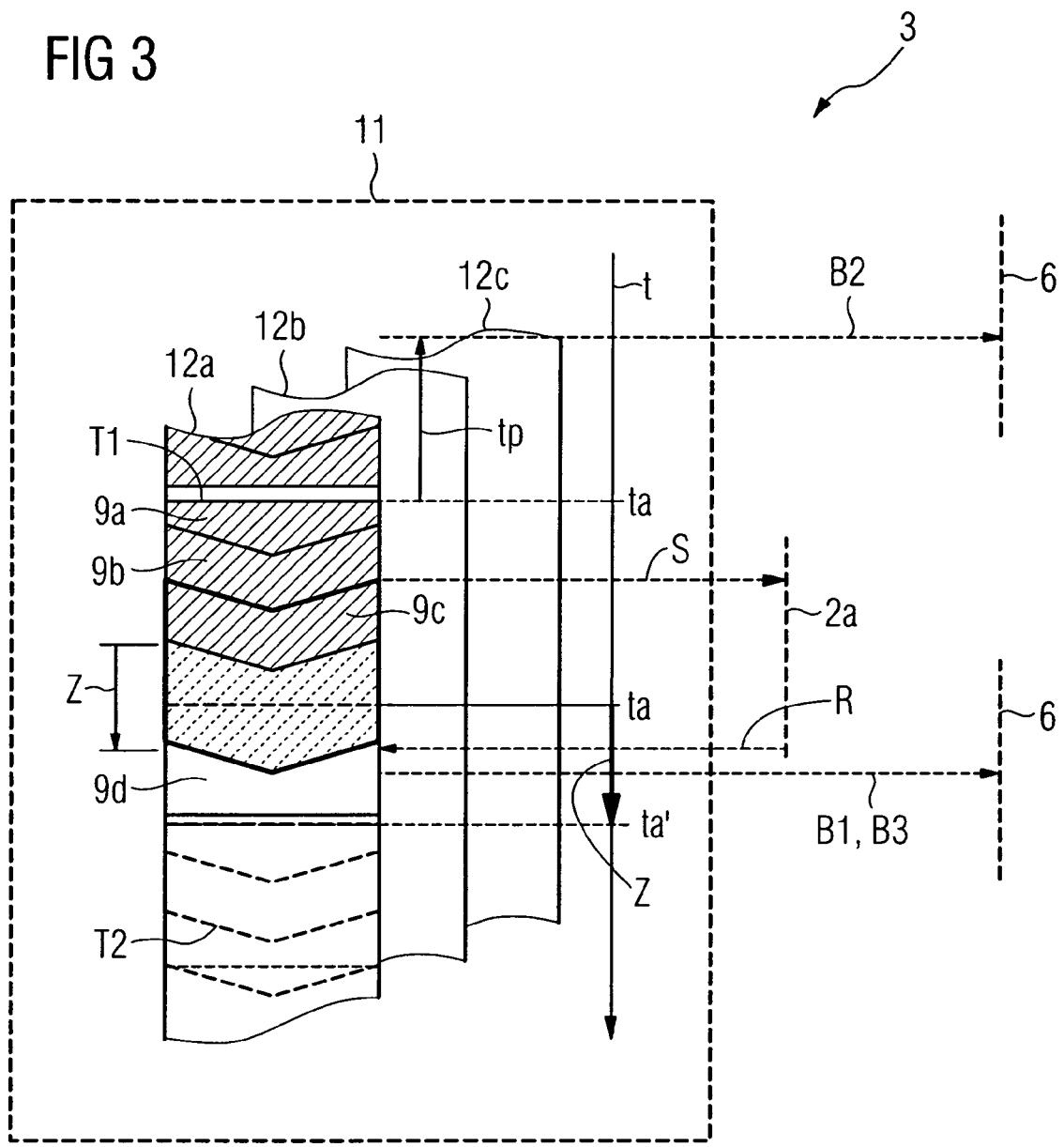
FIG. 3, in a further function chart, shows the appointment-scheduling module of FIG. 1 in a dynamic appointment adaptation.

In hospital settings, however, frequent and sometimes serious deviations from the actual treatment time, compared to the predetermined duration tv assigned to a standardized procedure 8a-8c, are unavoidable. One such case is shown as an example in FIG. 3. Here, performing the procedure step 9 for the appointment T1 takes approximately three times the specified time assigned to it. For dynamically adapting the subsequent appointments, in particular the next appointment T2, the appointment-scheduling module 3, from the feedback signal R, calculates the actual duration for performance of the procedure step 9c of the appointment T1. From the difference between the actual performance and the specified time for this procedure step 9c, the appointment-scheduling module 3 furthermore calculates the time lag Z by which the appointment schedule 11 in the example shown is now behind. The appointment-scheduling module 3 then postpones the next procedure step 9d with the appointment T1 by the amount of this time lag Z. Moreover, in place of the original starting times ta for all the following appointments T2, starting times ta' that have been corrected by the amount of the time lag Z are now set. The affected patient is automatically informed of the change in appointment by a message B1, forwarded to the appropriate communications units 6 by the appointment-scheduling module 3.

To prevent patients that are to be treated from having to be informed personally each time there is a change in appointment, possibly overloading a patient with more and more changes of appointment, it is optionally provided that the communications unit 6 assigned to a patient to be treated in an appointment is sent a message B2 only a single time, specifically prior to the properly set starting time ta by the amount of a predetermined lead time tp. Since in a hospital, a patient can be called up comparatively spontaneously for a given treatment, this lead time tp can be selected to be comparatively short, so that the risk of a further postponement of the appointment schedule 11 within this short lead time tp is comparatively slight. The likelihood of long waiting times for a patient is thus minimized. On the other hand, expediently each time there is a change in the appointment schedule 11, a corresponding message B3 with the updated appointment schedule 11 is output to a communications unit 6, where the information can call up information on the current appointment schedule 11 as needed, for instance on an information screen operated on the basis of HTML documents or screen text.

The time management system 1 preferably includes a locating system 13, shown schematically in FIG. 4, for locating patients, transporting devices, and medical products, and for generating corresponding feedback signals R once a patient, transport system, or product has been located. The locating system 13 is based on RFID technology and includes a number of RFID signal transducers 14a, 14b and RFID reader units (hereinafter reader units for short) 15a, 15b.

Each RFID signal transducer 14a, 14b is an (optionally active, but preferably passive) electrical oscillating circuit in the radiowave frequency range, which contains a predetermined item of information that is read out by electromagnetic interaction by each reader unit 15a, 15b of the locating system 13 when the RFID signal transducer 14a, 14b is kept in the sphere of influence of the reader unit 15a, 15b. The information associated with an RFID signal transducer 14a, 14b is configurable, and in particular it can be changed or deleted.

The RFID signal transducers 14a, 14b are mobile and are each assigned to one patient 16, one transporting device, or one medical product package, while the reader units 15a, 15b are stationary, or in other words are assigned to a particular examination station 2a-2c of the hospital.

In the example shown, a first RFID signal transducer 14a is integrated into a wristband and is secured to a wrist of the patient 16. A further RFID signal transducer 14b is embodied as a label and is applied to a product package 17. Other RFID signal transducers may be integrated in trolleys or the like, for instance.

One reader unit 15a is located at an entrance or exit of a room, especially a waiting room, assigned to one of the examination stations 2a. A further reader unit 15b is associated, as a handheld unit, with a control computer 18 in the examination station 2a.

By readout of the RFID signal transducers 14a, 14b by one of the reader units 15a, 15b, it is ascertained when the patient 16 is passing the reader unit 15a, by entering or leaving the waiting room, for instance, changing room, or treatment room that is associated with this reader unit 15a. This information is fed back to the appointment-scheduling module 3 by the respective reader unit 15a, 15b in the form of a suitable check-back signal R and is assessed for dynamic adaptation of appointment scheduling. Also by means of the reader unit 15b, it is ascertained when and to what extent medical products are being used for the treatment station 2a, and so forth.

It is therefore intended that the foregoing detailed description be regarded as illustrative rather than limiting, and that it be understood that it is the following claims, including all equivalents, that are intended to define the spirit and scope of this invention.

We claim:

1. A time management system for medical treatments comprising:

at least one treatment station having a first processor and a first memory coupled therewith; and a central server computer having a second processor and a second memory coupled therewith in communication with the at least one treatment station via a data network and comprising an appointment-scheduling module stored in the second memory and executable by the second processor and coupled with the at least one treatment station, the appointment-scheduling module being operative to cause the second processor of the central server to store a plurality of appointments in the second memory, each of the plurality of appointments being assigned to at least one medical procedure specified in view of one of the at least one treatment station and characterized by a predetermined duration, wherein the at least one medical procedure comprises a plurality of procedure steps; and further wherein:

the first processor of the at least one treatment station is operative to output, upon completion of each of the plurality of procedure steps of the at least one medical procedure of the assigned appointment, a check-back signal to the appointment scheduling module indicative thereof via the data network and, in response thereto, the appointment scheduling module is operative to cause the second processor to adapt subsequent of the plurality of appointments on the basis of at least one of the check-back signals;

the appointment scheduling module being further operative to cause the second processor of the central server to formulate each of the plurality of procedure steps of the at least one medical procedure assigned to the appointment in the form of a DICOM-standard-compatible planned procedure step; and the first processor of the at least one treatment station being further operative to generate the check-back signal based on each of the plurality of procedure steps that has been performed, the check-back signal being in the form of a DICOM-standard-compatible performed procedure step.

2. The time management system according to claim 1, wherein the at least one medical procedure is specified to the appointment-scheduling module for the at least one treatment station in view of the assigned predetermined duration.

3. The time management system according to claim 1, further comprising a locating system for generating the check-back signal, the locating system comprising one of a bar code system or radio frequency identification (RFID) system.

4. The time management system according to claim 3, wherein the locating system further comprises at least one RFID signal transducer and at least one RFID reader unit, the RFID reader unit being operative to generate the check-back signal when the associated RFID signal transducer is read out.

5. The time management system according to claim 4, wherein the at least one RFID signal transducer comprises a mobile part and the at least one RFID reader is characterized as being substantially stationary.

6. The time management system according to claim 5, wherein at least one of the at least one of the RFID signal transducers is capable of being assigned to one of a patient, a transporting device, or a medical product.

7. The time management system according to one of claim 1, wherein the appointment-scheduling module is operative to cause the second processor of the central server to automatically select the assigned starting time for the appointment, in the course of storing an appointment for a medical procedure in the memory.

8. The time management system according to one of claim 1, wherein the appointment-scheduling module is further operative to, in response to dynamically adapting subsequent of the plurality of appointments, cause the second processor of the central server to automatically informing a patient to whom the dynamically adapted appointment was assigned.

9. The time management system according to one of claim 1, wherein the appointment-scheduling module is operative to cause the second processor of the central server to automatically inform a patient, who has been assigned an appointment, of a predetermined lead time before an assigned starting time for the appointment.

10. A method of managing time for medical treatments, the method comprising:

providing at least one treatment station and a central server in communication therewith, the central server computer comprising a processor and a memory coupled therewith, the central server computer further comprising an appointment-scheduling module stored in the memory and executable by the processor and further coupled with the at least one treatment station via a data network;

storing by the appointment-scheduling module in the memory of the central server computer, a plurality of appointments, each of the plurality of appointments being assigned to at least one medical procedure specified in view of one of the at least one treatment station and characterized by a predetermined duration, wherein the at least one medical procedure comprises a plurality of procedure steps, each of the plurality of procedure steps of the at least one medical procedure being assigned to the appointment in the form of a DICOM-standard-compatible planned procedure step; and outputting, by a processor of the at least one treatment station upon completion of each of the plurality of procedure steps of the at least one medical procedure of the assigned appointment, a check-back signal to the appointment-scheduling module of the central server computer indicative thereof, the check-back signal being in the form of a DICOM-standard-compatible performed procedure step, and, in response thereto, adapting, by the processor of the central server computer, subsequent of the plurality of appointments on the basis of the at least one of the check-back signals.

* * * * *